US008132962B1

(12) United States Patent
Feller

(10) Patent No.: US 8,132,962 B1
(45) Date of Patent: Mar. 13, 2012

(54) ASYMMETRIC SPECIFIC HEAT METER

(76) Inventor: Murray F Feller, Micanopy, FL (US)

( * ) Notice: Subject to any disclaimer, the term of this patent is extended or adjusted under 35 U.S.C. 154(b) by 0 days.

(21) Appl. No.: 12/941,101

(22) Filed: Nov. 8, 2010

(51) Int. Cl.
G01K 17/00 (2006.01)
(52) U.S. Cl. ......................................... 374/29
(58) Field of Classification Search ............... 374/29
See application file for complete search history.

(56) References Cited

U.S. PATENT DOCUMENTS

| 4,813,270 | A | 3/1989 | Baillie |
| 6,023,969 | A | 2/2000 | Feller |
| 6,241,383 | B1 | 6/2001 | Feller |
| 7,775,706 | B1 | 8/2010 | Feller |
| 2005/0058177 | A1* | 3/2005 | Leonhardt ................. 374/16 |

* cited by examiner

Primary Examiner — Lisa Caputo
Assistant Examiner — Mirellys Jagan
(74) Attorney, Agent, or Firm — David Kiewit

(57) ABSTRACT

An asymmetric heat flux sensor has two sensing surfaces separately thermally coupled to the end plates of a thermoelectric module so that one is heated and the other cooled. The heated sensing surface is constrained to have a wettable area much larger than the area of the cooled sensing surface. This allows the heated sensing surface to be nearly the same temperature as the fluid ambient while providing a relatively large temperature differential. Because bubbles, which degrade a heat flux measurement, form preferentially on a heated surface, the asymmetric design avoids bubble formation and hence provides enhanced accuracy.

5 Claims, 2 Drawing Sheets

ASYMMETRIC SPECIFIC HEAT METER

BACKGROUND OF THE INVENTION

The present invention deals generally with calorimetry and more specifically with apparatus and method for improving heat flux measurements by defining and controlling the sensing area across which a heat flux occurs.

Related subject matter is addressed in the inventor's U.S. patent application Ser. No. 12/941,099 entitled "Specific Heat Meter with Improved Accuracy" filed on even date herewith.

BACKGROUND INFORMATION

The accuracy of instruments used to measure the specific heat of heat transfer fluids is limited by the accumulation of bubbles, debris or loose surface films on an active measurement surface. All of these contaminants reduce the effective area contacting the fluid and thereby reduce the amount of heat transferred to the fluid. Thus, these contaminants lead to the measured specific heat of the fluid being less than the true value.

In some known measurement methods chemicals are added to a sample of the working fluid to reduce the formation or attachment of bubbles. This approach is undesirable because the specific heat of the sample may be changed from that of the working fluid.

The heat transfer surfaces may also be manually wiped clean and/or abraded prior to each measurement. Variations in the results of manual cleaning also lead to uncertainty in the reliability of the subsequent specific heat measurement. Moreover, manual approaches are not applicable if specific heat is to be monitored automatically over an extended time interval or if a heat flux instrument is used to measure heat transfer to a flowing fluid, as is commonly done in heat metering applications.

The specific heat of a working fluid may be determined in a static measurement by withdrawing a sample of the fluid from a heat exchange system and placing it in a sample chamber. Alternately, the specific heat may be determined from sensors immersed in a flowing fluid as taught by the inventor in his U.S. Pat. No. 7,775,706, the disclosure of which is incorporated herein by reference. Moreover, as described in U.S. Pat. No. 7,775,706, because a heat flux probe is responsive to any thermal exchange with a working fluid, and these exchanges are enhanced if the fluid is moving, a heat flux probe can be used for making flow rate measurements. Such measurements, being responsive to both the specific heat of the liquid and its flow rate, are particularly useful for making heat transfer measurements as is done in BTU meters.

BRIEF SUMMARY OF THE INVENTION

In his related U.S. patent application Ser. No. 12/941,099 for a "Specific Heat Meter with Improved Accuracy", filed on even date herewith, the inventor teaches that accumulation of bubbles, debris or loose films may be reduced or eliminated by using an agitator to cause relative motion between a working fluid and an active surface of a specific heat sensor, or by using electrolytic cleaning of an electrically conductive heat transfer surface. Alternately, the two cleaning mechanisms can be used in combination.

In experimenting with thermoelectric (TEM) based heat flux sensors having two sensing surfaces, the inventor observed that bubbles formed predominately at the heated sensing surface of the TEM. The bubbles have a lower thermal conductivity than the liquid thereby reducing the effective area of that surface and leading to an erroneously low measured specific heat. The other, cooled, sensing surface typically remained free of bubbles, thus suggesting that improved measurement quality could be obtained by concentrating efforts aimed at removal of bubbles, debris and loose films primarily on the hotter sensing surface.

The inventor also noted that the effect of bubble formation at the heated sensing surface could be compensated for by increasing the area of the heated surface over that of the cooled surface. Moreover, if the area of the cooled sensing surface is reduced relative to the heated surface, the TEM produces a larger differential temperature for a fixed power input.

One aspect of the present invention is that it provides heat flux measurement apparatus comprising a TEM device having first and second end plates, which are typically parallel and facing each other. The first of these end plates is thermally coupled by means of a first thermal conductor to a first sensing surface having a first wettable area substantially larger than the area of the first end plate. The second of these end plates is thermally coupled by means of a second thermal conductor to a second sensing surface having a wettable area substantially less than the area of the second end plate. In operation of this device, the TEM is selectively electrically powered so as to heat the first end plate while cooling the second one.

Another aspect of the present invention is that it provides heat flux apparatus comprising a TEM device having first and second end plates. In this apparatus the first end plate is thermally coupled to a first sensing surface having a first wettable area and the second end plate is thermally coupled to a second sensing surface having a second wettable area. The second of these wettable areas is substantially smaller than the first wettable area. In operation of this device, the TEM is selectively electrically powered so as to heat the first end plate while cooling the second one.

Yet another aspect of the invention is that it provides a method of measuring a specific heat of a fluid. This method is carried out by providing an asymmetric probe having two sensing surfaces of substantially disparate areas. Each of the sensing surfaces is coupled to a different one of the two end plates of a TEM. The probe is immersed in the fluid and the TEM is energized by an electrical power supply having a polarity chosen so that the larger of the two sensing surfaces is heated and the smaller of the two sensing surfaces is cooled. The TEM's response to being energized is measured to determine the specific heat. As described in the inventor's U.S. patent application Ser. No. 12/941,099 entitled "Specific Heat Meter with Improved Accuracy" filed on even date herewith, there are multiple approaches to measuring a TEM's response to being energized. Some of these focus on supplying a controlled amount of energy to the TEM and measuring a temperature differential arising therefrom. Others focus on measuring the amount of energy required to create a selected temperature differential at its sensing surfaces.

Those skilled in the art will recognize that the foregoing broad summary description is not intended to list all of the features and advantages of the invention. Both the underlying ideas and the specific embodiments disclosed in the following Detailed Description may serve as a basis for alternate arrangements for carrying out the purposes of the present invention and such equivalent constructions are within the spirit and scope of the invention in its broadest form. Moreover, different embodiments of the invention may provide various combinations of the recited features and advantages of the invention, and that less than all of the recited features and advantages may be provided by some embodiments.

DETAILED DESCRIPTION OF A PREFERRED EMBODIMENT

Figure 1:
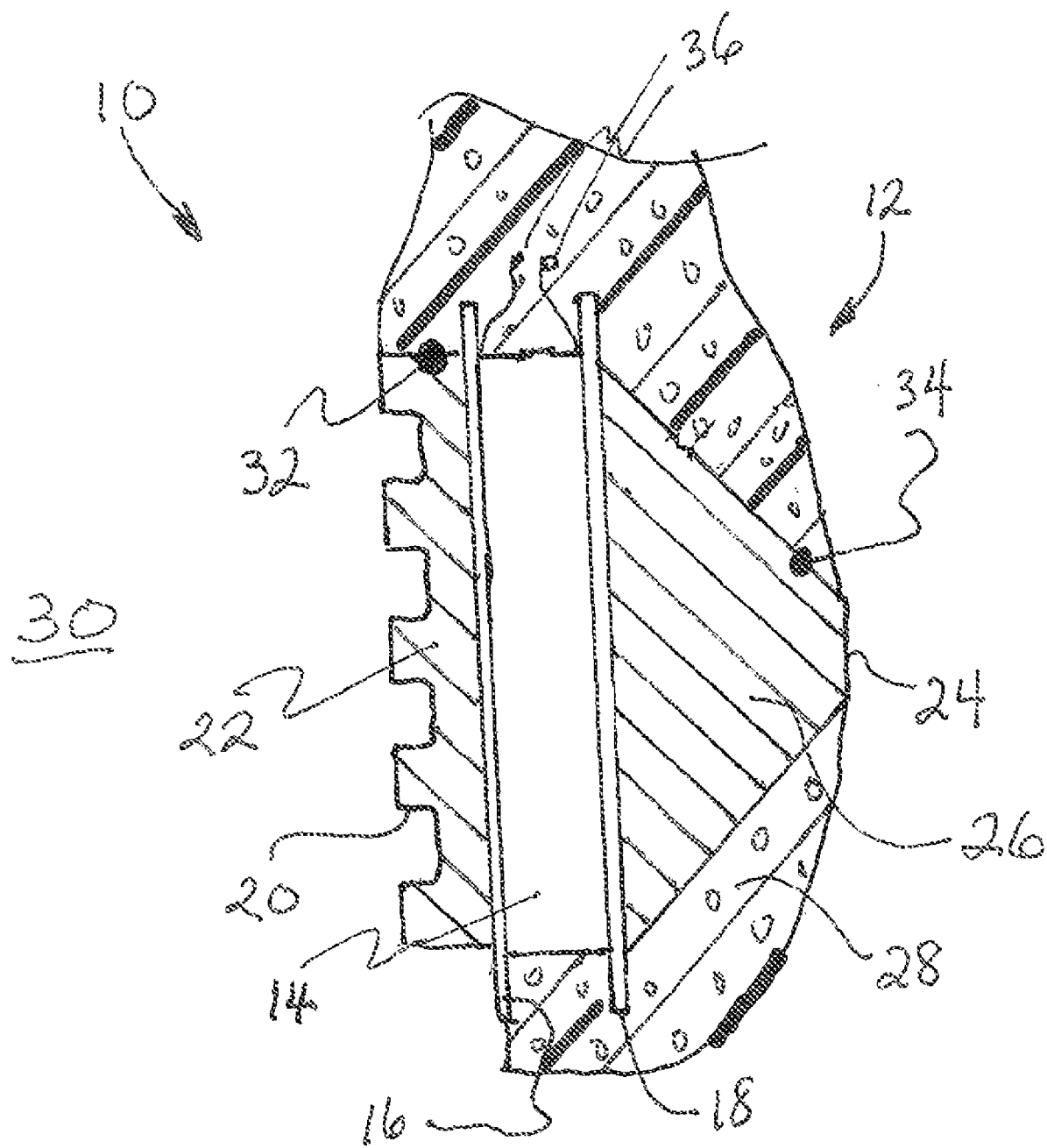
FIG. 1 is a partly schematic cross-sectional view, from which lead wires have been omitted in the interest of clarity of presentation, of a sensing head portion of a heat flux sensor of the invention.

Turning now to FIG. 1, one finds a partially schematic cross sectional depiction of a preferred heat flux sensing element 10 of the invention. A partially depicted probe 12 has a sensing head comprising a thermoelectric module (TEM) 14 of a known sort having a plurality of thermocouples arrayed between two alumina end plates 16, 18. Metallization patterns (not shown) on the internal facing sides of the end plates provide electrical connections to the thermocouples, which are electrically connected in series and physically arrayed parallel to each other so that when a selected voltage is applied to the TEM 14 all of the hotter sides of the thermocouples abut one of the plates and all of the colder sides abut the other.

The end plate 16 that is selected to be heated in operation is preferably thermally coupled to a sensing surface 20 that has, when the sensor is in use, a wetted area substantially larger than that of the cooled end plate 18 of the TEM. In the depicted preferred embodiment, this disparity in area is provided by thermally coupling the heated end plate to a finned body 22 formed from a material that is a good thermal conductor. In a preferred embodiment, the finned thermally conducting member was made of copper. The reader should understand both that many other thermal conductors may be used instead of copper and that, although many good thermal conductors are also electrical conductors, there is no requirement that the thermally coupling member be an electrical conductor.

Correspondingly, the plate 18 that is selected to be cooled in operation is preferably thermally coupled to a sensing surface 24 that, when the sensor is in use, is smaller than the cooled end plate of the TEM 14. In the depicted embodiment, the cooled end plate is thermally coupled to the fluid 30 by a domed, frusto-conical or frusto-pyramidal body 26 formed of a good thermal conductor (e.g., copper) and embedded in a thermal insulator 28 so that heat transfer between the cold plate 18 and the fluid 30 is constrained to occur only over a small exposed area. Although a thermal coupling member 26 is preferred, it is possible to use a small portion of the external surface of the cooled end plate as the cooled sensing surface. In such an arrangement, the balance of the cooled end plate is thermally isolated from the working fluid by suitable means, such as coating most of cooled end plate with an adhesive foam. In a preferred embodiment a rigid and durable insulation was made by mixing small hollow glass balls into an uncured epoxy resin at a 4:1 ratio.

The skilled reader will appreciate that there are many mechanical arrangements for providing a heated sensing surface that is larger than the corresponding heated plate as well as for providing a cooled sensing surface that is smaller than the corresponding cooled end plate. These arrangements include, but are not limited to, spacing the heated and cooled sensing surfaces that contact the fluid apart from each other by means of at least one heat pipe, and using a pipe wall or fitting as the heated sensing surface.

It may be noted that although in the depicted embodiment the heated sensing surface 20 is larger than the corresponding end plate 16 and the cooled sensing surface 24 is smaller than the corresponding cooled end plate 18, neither of these constraints is required. In some applications, an external surface of the heated end plate 16 of the TEM 14 may be directly exposed to the fluid so that the associated thermal conductor is unnecessary. What is required for the invention is that the wetted heated sensing area be substantially larger than the wetted cooled sensing area—e.g. preferably at least five times larger. In the depicted preferred embodiment, the areal ratio between the two sensing surfaces is on the order of 50:1 to 100:1.

Although the asymmetric heat flux sensor 10 of the invention is intended to minimize problems with bubbles, contaminant films and the like, these deleterious effects may still occur. Correspondingly, one may provide an electromechanical agitator (not shown) and/or electrolytic activation (not shown) of the wetted surfaces as taught in the inventor's U.S. patent application Ser. No. 12/941,099 for a "Specific Heat Meter with Improved Accuracy" filed on even date herewith, the disclosure of which is herein incorporated by reference.

There are several ways to measure the TEM-induced temperature difference across the two surfaces in contact with a working fluid. Although the TEM-generated voltage alone may be used for this function, a preferred approach is to provide separate temperature sensors 32, 34 adjacent each of the sensing surfaces and a temperature sensing connection 36 to the TEM 14. The sensors 32, 34 may be of any appropriate sort such as a platinum resistive detector or a semiconducting temperature sensor. This approach allows for direct measurement of a temperature difference that can control the power to the TEM for regulating the differential temperature of the conductors. Furthermore, the difference between the differential temperatures derived from the two temperature sensors 32, 34 and from the TEM sensing connection 36 may be utilized. This approach offers the advantages of detecting, with the TEM generated voltage, the differential temperature across the conductors and their thermal conducting paths as an indication of the heat being transferred to the fluid and eliminating the effect of the heat transfer conducted within the TEM between its heated and cooled surfaces.

Figure 2:
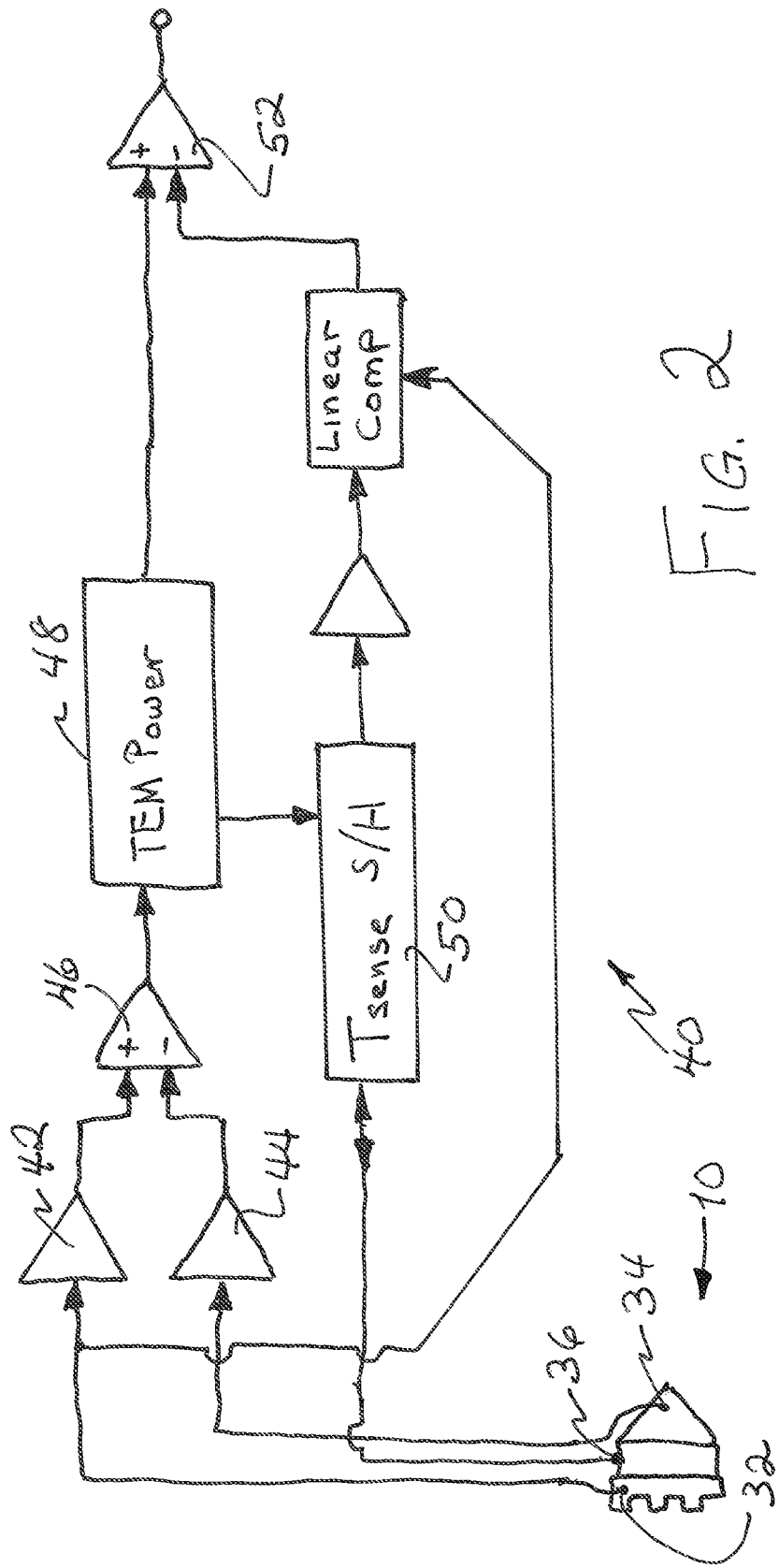
FIG. 2 is a schematic block diagram depicting a measurement system using the sensor of FIG. 1.

Turning now to FIG. 2 one finds a schematic block diagram of a sensor 10 and a processing circuit 40. Signals from temperature sensors 32, 34 at both sides of the TEM 14 are input into amplifiers 42, 44 having respective outputs that are input to a differential amplifier 46 that supplies a net temperature differential signal to a TEM power controller 48 which powers the TEM to maintain a constant net differential temperature. The TEM is powered continuously except for small intervals during which its open circuit voltage is measured at the sensing connection 36 by a sample and hold circuit 50. This TEM-generated voltage corresponds to the temperature across the TEM and, when amplified, can be input to the inverted terminal of an output amplifier 52 to compensate for temperature drops and for thermal losses.

The net differential temperature is preferably maintained over the full range of heat transfer experienced by the heated and cooled sensing surfaces for a particular application. The TEM current is controlled to maintain this differential and is the primary indicator of power supplied to the TEM. Any deviations that may result from temperature drops within the thermal conductors can be compensated for by output signal processing as they are measurable and repeatable.

In general, the average temperature indicated by the voltage generated by a TEM is not linear over a large temperature range. Hence, a correction signal corresponding to the temperature of the large area heat sinking conductor 22, which is preferably maintained essentially at the temperature of the fluid 30, is used for linear compensation with temperature. The TEM may also have other nonlinearities associated with its operation that can also be compensated for in the circuit of FIG. 2 because its temperature and current signals are available for such use. Thus, signals primarily representing the current into the TEM and the compensated TEM-generated differential voltage and temperature are supplied to the output differential amplifier 52 which provides the corrected output signal.

An offset is provided in either the positive (shown) or negative input of the output amplifier 52 so that the output signal calibration matches the application. For example, the offset would be selected to produce a zero output at zero flow rate for a flow meter application or a specific level for a specific heat measurement. The output signal is primarily responsive to the heat flux required to produce the differential temperature at the thermal conductors and is minimally responsive to internal TEM thermal conduction.

The preferred sensor has only a relatively small cooled sensing area 24 exposed to the liquid and can operate with small (e.g., one degree centigrade) TEM temperature differentials so that a relative small amount of heat transfer to the fluid takes place. Additionally, the TEM operates as an efficient heat pump rather than as a power dissipating resistor. Relatively little power is therefore consumed by the probe in making specific heat or flow rate measurements. This feature, plus the relative immunity to bubble formation and surface contamination enables meters of the present invention to be used in a wider variety of applications than previously possible with thermally responsive meters.

Although the present invention has been described with respect to several preferred embodiments, many modifications and alterations can be made without departing from the invention. Accordingly, it is intended that all such modifications and alterations be considered as being within the spirit and scope of the invention as defined in the attached claims.

The invention claimed is:

1. An apparatus for measuring heat flux when wetted by a fluid, the apparatus comprising:
a thermoelectric device comprising first and second end plates, the first end plate thermally coupled by means of a first thermal conductor to a first sensing surface having a first wettable area substantially larger than the area of the first end plate, the second end plate thermally coupled by means of a second thermal conductor to a second sensing surface having a second wettable area substantially less than the area of the second end plate.

2. The apparatus of claim 1 wherein the second wettable area is no more than 20% of the first wettable area.

3. The apparatus of claim 1 wherein the first and second thermal conductors comprise respective metal members.

4. The apparatus of claim 1 wherein at least one of the two sensing surfaces comprises a metal film disposed on the associated thermal conductor and wherein a thermal insulator is disposed over most of the second end plate.

5. The apparatus of claim 1 wherein at least the second sensing surface is electrically conductive, the apparatus further comprising a power supply operable to selectively supply a respective voltage to each of the at least one electrically conducting surface.

* * * * *